(12) United States Patent
Bowman et al.

(10) Patent No.: US 6,506,909 B1
(45) Date of Patent: Jan. 14, 2003

(54) METHOD OF MAKING TRIMETHYLENE CARBONATE

(75) Inventors: Mark P. Bowman, New Kensington, PA (US); Charles B. Kreutzberger, Harrison City, PA (US)

(73) Assignee: PPG Industries Ohio, Inc., Cleveland, OH (US)

( * ) Notice: Subject to any disclaimer, the term of this patent is extended or adjusted under 35 U.S.C. 154(b) by 0 days.

(21) Appl. No.: 10/029,729

(22) Filed: Dec. 20, 2001

(51) Int. Cl.$^7$ ............................................ C07D 319/04
(52) U.S. Cl. ...................................... 549/228
(58) Field of Search ........................ 549/228

(56) References Cited

U.S. PATENT DOCUMENTS

| | | | |
|---|---|---|---|
| 4,365,055 A | 12/1982 | Madigan | 528/371 |
| 4,384,115 A | 5/1983 | Renga | 544/97 |
| 5,023,346 A | * 6/1991 | Schon | |
| 5,091,543 A | 2/1992 | Grey | 549/228 |
| 5,212,321 A | 5/1993 | Muller et al. | 549/228 |

FOREIGN PATENT DOCUMENTS

| | | |
|---|---|---|
| JP | 94126269 | 6/1994 |
| JP | 94126271 | 6/1994 |

OTHER PUBLICATIONS

T. Ariga et al., *Macromolecules*, "Cationic Ring–Opening Polymerization of Cyclic Carbonates with Alkyl Halides to Yield Polycarbonate without the Ether Unit by Suppression of Elimination of Carbon Dioxide", 30 (1997) pp 737–743.

W. H. Carothers et al., Studies on Polymerization and Ring Formation. III Glycol Esters of Carbonic Acid:, *J. Am. Chem. Soc.*, 52 (1930) pp 314–326.

D. Saunders et al., "The Reaction of Oxygen Atoms with Tetrafluoroethylene", *J. Am. Chem. Soc.*, 87 (1965) pp 2088–2092.

U.S. Ser. No. 10/029,728, filed Dec. 20, 2001, Method of Making Trimethylene Carbonate, Mark P. Bowman and Charles B. Kreutzberger.

* cited by examiner

*Primary Examiner*—Joseph K. McKane
*Assistant Examiner*—Sonya Wright
(74) *Attorney, Agent, or Firm*—Dennis G. Millman

(57) ABSTRACT

A method of synthesizing trimethylene carbonate is disclosed involving (a) reacting 1,3-propanediol and a compound chosen from phosgene and bis-chloroformates to form a polycarbonate intermediate having the structure:

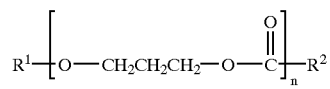

wherein n is at least 2; $R^1$ is an end group chosen from H, $R^3$-Cl, $R^3$-OH and —C(O)Cl, where $R^3$ is $C_1$–$C_6$ linear or branched alkyl and $R^2$ is an end group chosen from —$OCH_2CH_2CH_2Cl$, —$OCH_2CH_2CH_2OH$ and Cl; and (b) providing a combination of temperature and pressure corresponding to vapor phase conditions for trimethylene carbonate.

37 Claims, 1 Drawing Sheet

METHOD OF MAKING TRIMETHYLENE CARBONATE

BACKGROUND OF THE INVENTION

1. Field of the Invention

The present invention is directed to a method of producing cyclic carbonic acid esters. More particularly, the present invention involves a low cost method of producing trimethylene carbonate.

2. Description of the Prior Art

Cyclic carbonic acid esters are used, for example, as building blocks of potentially biodegradable polymers. A particular cyclic carbonic acid ester, trimethylene carbonate (1,3-dioxan-2-one) may be used in a variety of applications, such as for surgical stitching material, vessel implants and apparatus for osteo-synthesis. Trimethylene carbonate is a desirable monomer to use because of its unique property of not decreasing in volume on polymerization.

Trimethylene carbonate may be used as a monomer in the synthesis of poly(trimethylene carbonate) polyols, which are used in flexibilizing acrylic melamine coatings. Trimethylene carbonate may also be used to make surgical sutures and modified polyurethane elastomers. Poly(trimethylene carbonate) polyols improve both ambient and low temperature flexibility and reduced the viscosity of urethane coatings formulated with selected commercial acrylic polyols.

For industrial production of trimethylene carbonate, it is desirable to find a method of synthesis yielding cyclic carbonates that can be produced in high yields, by a relatively simple industrial process. Numerous methods are known for producing carbonic acid esters such as trimethylene carbonate. For example, the trans-esterfication of diethylcarbonate with 1,3-propanediol in the presence of sodium or sodium methoxide to obtain trimethylene carbonate is one of the oldest methods of production (W. H. Carothers and F. V. Natta, J Am. Chem. Soc. 52 (1930) 322), but the low yield makes this method unattractive for industrial use.

U.S. Pat. No. 5,212,321 to Muller et al. discloses a method for producing trimethylene carbonate wherein 1,3-propanediol is reacted with diethylcarbonate in the presence of zinc powder, zinc oxide, tin powder, tin halide or an organo-tin compound at an elevated temperature. However, the Muller et al. process is very expensive as the process the separation, isolation and disposal of residues and catalysts, which are time consuming and expensive.

U.S. Pat. No. 5,091,543 to Grey discloses a method of preparing five- and six-membered cyclic carbonates. The method involves reacting a 1,2- or 1,3-diol with an acyclic diester of carbonic acid in the presence of a catalyst selected from alkylammonium salts, tertiary amines, and ion-exchange resins containing alkylammonium or tertiary amino groups. Cyclic carbonates free of carbonate based product by-products are obtained. However, the Grey process is also very expensive as the process requires the use of reactors made from materials of construction that will not corrode when exposed to the halide ions in the process. Isolation and disposal of residues and catalysts are also time consuming and expensive.

Another process used to prepare trimethylene carbonate involves reacting 1,3-propanediol with urea in the presence of zinc based catalysts. This type of process is described, for example, in Japanese Patent Nos. 7-330686 and 7-330756. The process requires expensive and time consuming isolation, recovery and recycling of the catalyst.

Trimethylene carbonate has also been made by reacting 1,3-propanediol with ethylchloroformate in the presence of two equivalents of triethylamine using tetrahydrofuran as a solvent (Toshiro Agriga et al., Macromolecules 30 (1997) 737). However this method produces trimethylene carbonate in low yield, and requires expensive and time-consuming recovery of the amine and the solvent.

Linear carbonate polymers can be prepared from carbonic dihalides and diols using catalytic amounts of nitrogen containing bases. U.S. Pat. No. 4,365,055 to Madigan, for example, discloses a method of preparing a carbonate based product by introducing phosgene to an anhydrous solution of at least one substituted or unsubstituted 1,3-propanediol in a solvent. A particular teaching of the Madigan patent is that coproduction of cyclic carbonates is reduced by the presence in the solution of a catalytic amount of a nitrogen-containing base such as pyridine. The method disclosed by Madigan et al. requires the use of catalytic quantities of nitrogen containing, hydrohalide salt-forming bases in order to produce linear carbonate polymers. The method according to Madigan is also expensive because it requires solvent removal.

There remains a need for a low cost method for producing trimethylene carbonate. A low cost method desirably involves production of trimethylene carbonate in relatively high yields. Further reductions in cost could be attained if trimethylene carbonate could be made without requiring use of catalysts or acid scavengers with their associated expenses for clean up and/or recycling or disposing of residues of catalyst material or hydrohalide salts. A combination of several or all of the desirable features would be even more desirable.

SUMMARY OF THE INVENTION

The present invention is directed to a method of synthesizing trimethylene carbonate comprising the steps of:

reacting 1,3-propanediol and either phosgene or a bis-chloroformate, without an HCl scavenger, to form a polycarbonate based intermediate having the

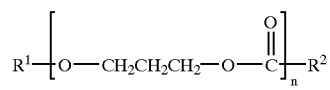

where n is at least 2, $R^1$ is an end group and can be H, $R^3$—Cl, $R^3$—H or —C(O)Cl, where $R^3$ is $C_1$–$C_6$ linear or branched alkyl and $R^2$ is an end group and can be —OCH$_2$CH$_2$CH$_2$Cl, —OCH$_2$CH$_2$CH$_2$OH or Cl; and applying a combination of temperature and pressure at which trimethylene carbonate will be in the vapor phase, generating trimethylene carbonate vapors.

The present invention advantageously provides a method for making trimethylene carbonate with efficient high yields. Some embodiments of the invention provide the additional advantage of not requiring use of catalysts or acid scavengers. Although not required, the use of catalysts or acid scavengers is not precluded in other embodiments of the method of the present invention.

DETAILED DESCRIPTION OF THE INVENTION

Figure 1:
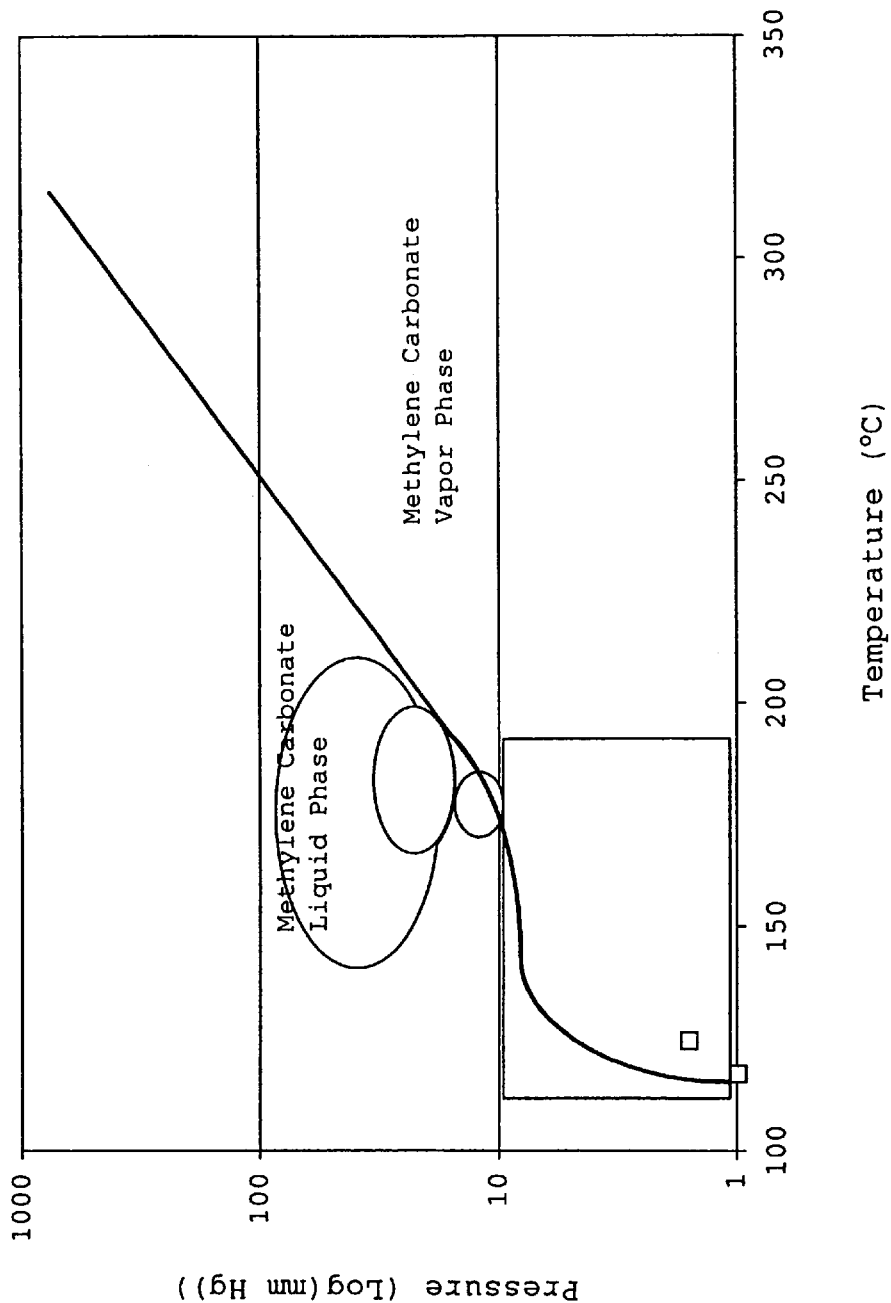
FIG. 1 is a plot of the relationship between the boiling temperature of trimethylene carbonate and pressure.

Unless otherwise indicated, all numbers or expressions referring to quantities of ingredients, reaction conditions, etc. used herein are to be understood as modified in all instances by the term "about." All references to pressure refer to absolute pressure unless otherwise indicated.

The method of synthesizing trimethylene carbonate of the present invention includes a first step of reacting 1,3-propanediol and either phosgene or a bis-chloroformate, without an HCl scavenger, to form a polycarbonate based intermediate having the general structure I:

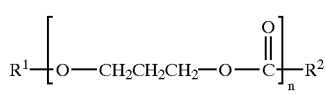
(I)

where n is the number of trimethylene carbonate units. The subscript n is an integer and can be any number. In an embodiment of the present invention, n is from 2 to 100,000 and may be from 2 to 1,000, typically, n is from 2 to 500, more typically from 2 to 250 and most typically from 3 to 100. When n is too high, the viscosity of the polycarbonate based product may be too high and it may become difficult to handle on an industrial scale. $R^1$ is an end group and can be H, $R^3$—Cl, $R^3$—OH or —C(O)Cl, where $R^3$ is $C_1$–$C_6$ linear or branched alkyl, and $R^2$ is an end group and can be —$OCH_2CH_2CH_2Cl$, —$OCH_2CH_2CH_2OH$ or Cl. Known methods can be employed to make the carbonate based intermediate.

In an embodiment of the present invention, the polycarbonate based intermediate may be prepared by reacting 1,3-propanediol and phosgene. The molar ratio of 1,3-propanediol to phosgene in the reactants is most efficiently at or near stoichiometric amounts, but theoretically a wide range can be used. For example, the reactant ratios of 1,3-propanediol to phosgene may range from 1.3:0.7 to 0.7:1.3, typically from 0.8:1.2 to 1.2:0.8, and most typically from 0.95:1.05 to 1.05:0.95.

When 1,3-propanediol and phosgene are used outside the stated ranges, the yield may be so low as to be impractical for industrial requirements.

In an embodiment of the present invention, a slight excess of 1,3-propanediol may be used. When an excess of 1,3-propanediol is used, the ratio of 1,3-propanediol to phosgene is from 1.0001:1 to 1.3:1, typically from 1.001:1 to 1.2:1, more typically from 1.01:1 to 1.1:1 and most typically from 1.01:1 to 1.05:1. The slight excess of 1,3-propanediol minimizes the formation of chloroformate end groups. When an excess of 1,3-propanediol is used, the resulting polycarbonate based intermediate may be a mixture with a minority of the composition represented by general structure 11 and a majority of the composition being represented by a polycarbonate based product with general structure III:

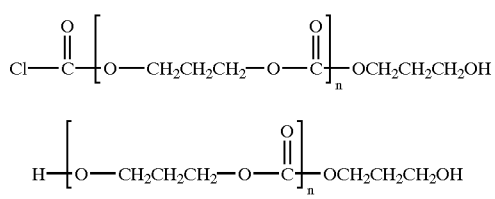
(II)

(III)

where n is defined as above.

In addition to phosgene, phosgene equivalents can be used in the present method. Phosgene equivalents that can be used in the present invention include, but are not limited to diphosgene and triphosgene. Phosgene equivalents decompose to form phosgene in situ, but are preferable in some cases due to their ease of handling on a commercial scale compared to phosgene.

The chloroformate end group in structure II of the intermediate is not preferred. The chloroformate end group can react with active hydrogen-containing compounds such as alcohols and water. Therefore intermediates having chloroformate end groups may continue to react during storage to generate hydrogen chloride and $CO_2$, which is preferably avoided.

The temperature at which the reaction of 1,3-propanediol and phosgene is carried out is not critical. For practical considerations, the reaction is typically carried out at a temperature of from −20° C. to 100° C., typically from −10° C. to 75° C., more typically from 0° C. to 50° C. and most typically from 0° C. to 25° C. When the temperature is below the stated ranges, especially below −20° C., the polymerization rate may be slower than desirable for industrial use. When the temperature is above the stated ranges, especially above 100° C., some of the 1,3-propanediol may react to form 1-chloro-3-propanol, which acts to "endcap" the polymer during polymerization, thus limiting the obtainable molecular weight of the polymer.

The temperature of the reaction vessel may be maintained at the polymerization temperature for a period of time sufficient to react 1,3-propanediol and phosgene to polycarbonate based product. During the reaction, hydrogen chloride is formed and is removed from the reaction vessel through a suitable condenser. Removal of hydrogen chloride may be aided through the use of reduced pressure and/or an inert gas sparge. A subnatant inert gas sparge is typically used. If hydrogen chloride is not rapidly removed as it is formed, hydroxy end groups may be converted to unwanted alkyl chlorides. Alkyl chlorides can act as chain terminators or "chain stoppers" during formation of the polycarbonate intermediates. In an embodiment of the present invention, the temperature of the condenser may be maintained at a suitable temperature to also condense any phosgene that has evaporated. In order to condense phosgene, a condenser temperature less than 8° C. (boiling temperature of phosgene), typically less than 0° C. has been found to be suitable.

The polymerization is typically run neat, i.e., containing only monomers and polymer. However, a suitable solvent may be used in the method of the present invention. Suitable solvents are those solvents that do not contain an active hydrogen. Suitable solvents include, but are not limited to, toluene, heptane and 1,2-dichloroethane.

The 1,3-propanediol and phosgene can be added to the reaction vessel in any order of addition. Typically, they are added simultaneously.

In an alternative embodiment poly(trimethylene carbonate) may be prepared by reacting 1,3-propanediol with the bis-chloroformate of 1,3-propanediol. The bis-chloroformate may be prepared by adding 1,3-propanediol to an excess of phosgene in an appropriate reaction vessel, forming a bis-chloroformate having general structure IV:

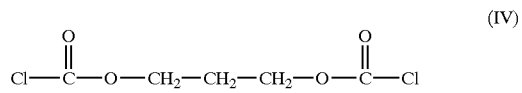
(IV)

The reaction may be run at a temperature of from −20° C. to 100° C., typically from −110° C. to 75° C., more typically from 0° C. to 50° C. and most typically from 0° C. to 25° C. When the temperature is below the stated ranges, especially below −20° C., the reaction proceeds slowly and may not be practical for industrial utilization. Above the stated temperature ranges, competing reactions are more likely to take place.

In addition to phosgene, phosgene equivalents can be used to prepare the bis-chloroformate. Phosgene equivalents that can be used to make the bis-chloroformate include, but are not limited to diphosgene and triphosgene.

In preparing the bis-chloroformates, the ratio of 1,3-propanediol to phosgene may be 1:1.7 to 1:10, typically 1:2.1 to 1:5 and most typically 1:2.1 to 1:3. At amounts of phosgene below those stated, a sufficient excess of phosgene may not be present and the yield of bis-chloroformate formed may be low. Higher amounts of phosgene are theoretically feasible, but can lead to higher costs due to greater efforts needed to separate the bis-chloroformate and to recover and recycle the phosgene.

In the embodiment utilizing a preliminary step of forming bis-chloroformate of 1,3-propanediol, polycarbonate intermediate may be prepared by adding 1,3-propanediol and the bis-chloroformate to a suitable reaction vessel. The ratio of 1,3-propanediol to the bis-chloroformate may be from 1.3:0.7 to 0.7:1.3, typically from 0.8:1.2 to 1.2:0.8 and most typically from 0.95:1.05 to 1.05:0.95.

When 1,3-propanediol and the bis-chloroformate are used outside of the stated ranges, the yield of carbonate based product may be too low to be practical for industrial use.

The polymerization is run at a suitable temperature to react 1,3-propanediol and the bis-chloroformate to form polycarbonate intermediate. The temperature can be from 0° C. to 100° C., typically from 0° C. to 75° C., more typically from 0° C. to 50° C. and most typically from 0° C. to 25° C. When the temperature is below the stated ranges, especially below 0° C., the polymerization rate may be slower than desirable for industrial use. When the temperature is above the stated ranges, especially above 100° C., some of the 1,3-propanediol may react to form 1-chloro-3-propanol, which acts to terminate chain growth during polymerization, thus limiting the obtainable molecular weight of the carbonate based intermediate.

The temperature is maintained for a period of time sufficient to react 1,3-propanediol and bis-chloroformate to form the carbonate based intermediate. The use of reduced pressure and/or an inert gas sparge facilitates the removal of hydrogen chloride, which minimizes unwanted side reactions.

The polymerization is typically run neat, i.e., containing only monomers and polymer. However, a suitable solvent can be used in the method of the present invention. Suitable solvents are those solvents that do not contain an active hydrogen. Suitable solvents include, but are not limited to, toluene, heptane and 1,2-dichloroethane.

After the polycarbonate intermediate is formed, it may be subjected to an optional preliminary heat treatment prior to being cracked to form trimethylene carbonate. The preliminary heat treatment serves to react and eliminate chloroformate end groups from the polycarbonate intermediate. The end group elimination generates hydrogen chloride. The conversion is aided by removal of the hydrogen chloride, which can be facilitated by introducing an inert gas to the polycarbonate intermediate and/or the application of reduced pressure. Any inert gas can be used. Suitable inert gasses include, but are not limited to nitrogen, neon, argon and helium. Nitrogen is a preferred inert gas. The use of vacuum can also assist removal of hydrogen chloride.

The preliminary heat treatment may involve temperatures up to the boiling temperature of trimethylene carbonate. The heat treatment can be carried out at temperatures as low as 50° C. or lower, but at lower temperatures the heat treatment may require an impractically long time to complete. Therefore, the heat treatment is typically carried out between 50° C. and 250° C. and most typically between 50° C. and 150° C. for a period of time sufficient to remove most chloroformate end groups. It is preferable to avoid chloroformate end groups in the subsequent process steps, but the presence of some chloroformate end groups can be tolerated. The removal of hydrogen chloride minimizes the occurrence of unwanted side reactions. The heat treatment may be from one hour to 12 hours, typically from one hour to 10 hours. The use of higher temperatures and longer times is useful to reduce the presence of chloroformate end groups to trace levels.

In an embodiment of the present invention, phosgene paper may be used to determine that the level of chloroformate end groups is sufficiently low. Phosgene test paper provides a color change indication of the presence of chloroformates. An example of phosgene paper that can be used in the present invention includes, but is not limited to, Chemcassette® SP test paper for phosgene available from MDA Scientific Inc., Lincolnshire, Ill.

Following the chloroformate heat treating step (if used) the polycarbonate intermediate is further heated in order to depolymerize (or "crack") and remove trimethylene carbonate. For this step it has been found advantageous to employ a combination of reduced pressure and elevated temperature at or near boiling conditions of trimethylene carbonate, thereby generating trimethylene carbonate vapors. FIG. 1 shows a plot approximating the relationship of the boiling temperature of trimethylene carbonate with pressure derived from several known data points. Vapor phase conditions for trimethylene carbonate include any combination of temperature and pressure to the right of the curve in FIG. 1.

The trimethylene carbonate vapor produced by the cracking step is removed from the reaction vessel and condensed. The condensation is accomplished by exposing the trimethylene carbonate vapor to a liquid phase condition (any location to the left of the curve in FIG. 1).

The cracking of the polycarbonate intermediate may optionally be augmented by the use of an appropriate catalyst. Cracking catalysts that can be used in the present invention include, but are not limited to zinc and its organic and inorganic salts and tin and its organic and inorganic salts. Preferred cracking catalysts include zinc powder; zinc oxides; tin powder; tin halides, such $SnCl_2$, and organo-tin compounds, such as dibutyltindiacetate.

The liquid trimethylene carbonate may be isolated for further processing. In an embodiment of the present invention, the condensed trimethylene carbonate is placed in a suitable vessel and is allowed to solidify. In order to subsequently use the trimethylene carbonate, the vessel is heated to melt the trimethylene carbonate. The vessel can be, but is not limited to a drum or a tote.

In an embodiment of the present invention, the liquid trimethylene carbonate may be solidified. Once solidified, the solid trimethylene carbonate can be processed into a suitable solid form for storage and use. For example, the solidified trimethylene carbonate may be milled into granular or powder form.

The trimethylene carbonate can be purified by distillation, crystallization or recrystallization. In the case of crystallization, the trimethylene carbonate is dissolved into an appropriate organic solvent, containing no active hydrogens. The solution is then cooled to a temperature at which trimethylene carbonate crystals precipitate. The trimethylene carbonate crystals are then recovered. A non-limiting example of a suitable solvent is acetone.

The present invention is more particularly described in the following Examples, which are intended to be illustrative only, since numerous modifications and variations therein will be apparent to those skilled in the art. Unless otherwise specified, all parts and percentages are by weight.

EXAMPLES 1–6

Examples 1–6 are comparative control reactions demonstrating that conventional phosgenation is an ineffective method to directly produce trimethylene carbonate.

EXAMPLE 1

This is an example of a conventional phosgenation in a solventless system. The reaction was carried out at atmospheric pressure in a glass reaction vessel equipped with a mixing means, heating mantle or ice bath, thermometer and condenser. Phosgene (49 g) was added over 50 minutes to 1,3-propanediol (40.9 g, 1.08 equiv.). The temperature was maintained at 7–19° C. A sample taken after the reaction period contained 6% trimethylene carbonate (based on 1,3-propanediol) and other higher boiling materials as determined by gas chromatography.

EXAMPLE 2

This is an example of conventional phosgenation using a normal mode of addition in 1,2-dichloroethane. The equipment used was as described in example 1.

The 1,3-propanediol (11.0 g) was added over 10 minutes to a solution of phosgene (I 8 g, 1.26 equiv.) in 1,2-dichloroethane (100 ml). The temperature was maintained at 20 58–71° C. A sample taken after the reaction period had 13% conversion to trimethylene carbonate (based on propanediol) as determined by gas chromatography.

EXAMPLE 3

This is an example of conventional phosgenation using an inverse mode of addition in 1,2-dichloroethane.

The equipment used was as described in example 1. Phosgene (24 g, 1.9 equiv.) was added over one hour to a solution of 1,3 propanediol (9.7 g) in 1,2-dichloroethane (100 ml). The temperature was maintained at 75° C. A sample taken after the reaction period had 5% conversion to trimethylene carbonate (based on 1,3-propanediol) as determined by gas chromatography.

EXAMPLE 4

This is an example of a conventional phosgenation method of co-feeding 1,3-propanediol and phosgene. The equipment used was as described in example 1. Phosgene (23 g, 1.7 equivalent) and 1,3-propanediol (10.4 g) were co-fed over a one-hour period to 1,2-dichloroethane. The temperature was maintained at 80° C. during the reaction period. A sample taken after the reaction period had 16% conversion to trimethylene carbonate (based on 1,3-propanediol) as determined by gas chromatography.

EXAMPLE 5

This is an example of a conventional higher temperature phosgenation run in chlorobenzene. The equipment used was as described in example 1. 1,3-propanediol (9.6 g) was added over 15 minutes to a solution of phosgene (23.8 g, 1.91 equiv.) in chlorobenzene (110 ml). The temperature was maintained at 111–125° C. during the reaction period. A sample taken after the reaction period had 16% conversion to trimethylene carbonate (based on 1,3-propanediol) as determined by gas chromatography.

EXAMPLE 6

This is an example of a conventional phosgenation utilizing toluene as a reaction solvent. The equipment used was as described in example 1. One equivalent of 1,3-propanediol (11.3 g) was slowly added dropwise over 50 minutes to a solution of 15 g of phosgene (1 equivalent) in 100 ml of toluene at room temperature. The crude product contained 3.3% converted starting material to trimethylene carbonate (based on 1,3-propanediol).

Examples 1–6 demonstrate that direct phosgenation of 1,3-propanediol produces trimethylene carbonate in very low, uneconomical yields. Regardless of the solvent, temperature or mode of addition utilized, direct phosgenation of 1,3-propanediol was found to be ineffective.

EXAMPLE 7

This is an example of the bis-chloroformate method of synthesizing a polycarbonate intermediate and subsequent conversion to trimethylene carbonate of the present invention. The equipment used was as described in example 1 except that a vacuum pump and a sparge line were also used.
Synthesis: bis-Chloroformate of 1,3-Propanediol The bis-chloroformate of 1,3-propanediol was prepared by adding 1,3-propanediol (101.0 g) over 90 minutes to a pool of phosgene (394 g, 3.00 equivalents). The temperature was maintained at 3–9° C. during the addition period. A nitrogen purge was used to remove hydrogen chloride from the reactor. A condenser (–40° C.) was used to prevent the loss of phosgene. The product was analyzed by gas chromatography to be 91.8% (by area) bis-chloroformate.
Polycarbonate Synthesis 1,3-Propanediol ($^2$6.5 g, 1.07 equivalent) and the bis-chloroformate of 20 1,3-propanediol (65.6 g) were co-fed to a flask over 90 minutes. The temperature was maintained at 50° C. and a pressure of 24 mm Hg. The temperature of the flask was then maintained at 50° C. for an additional four hours under vacuum (24 mm Hg). The mixture was heated and maintained at 75° C. for 100 minutes and further heated to 100° C. for 30 minutes while maintaining a pressure of 24 mm Hg. The vacuum was broken and a nitrogen sparge was introduced to the flask while maintaining the temperature at 50° C. for 16 hours. The polycarbonate contained primarily high molecular weight oligomers (n>5 as shown in structures I and II) as determined using gel permeation chromatography using a 120-cm PL-Gel 50-angstrom gel permeation column and visually estimating the chain length based on the chromatogram.
Synthesis of Trimethylene Carbonate A portion of the polycarbonate (25.2 g) with 0.7 g of added dibutyltindiacetate was cracked under vacuum. The flask was topped with a Vigreux distilling head. Distillate fractions were collected at:

1) 94–103° C. and 0.9 mm Hg (2.5 g, 57% trimethylene carbonate, pot temp. 193–205° C.), and
2) 105–108° C. and 0.9 mm Hg (19.9 g, 99% trimethylene carbonate, pot temp. 205–218° C.).

The overall recovery of trimethylene carbonate contained in the two distillate fractions, based on the polycarbonate charged, was 85% as determined by gas chromatography.

EXAMPLE 8

This is an example of the bis-chloroformate method of synthesizing a polycarbonate and subsequent conversion to trimethylene carbonate in accordance with the present invention. The bis-chloroformate was prepared as outlined in Example 7.

Polycarbonate Synthesis 1,3-propanediol (36.0 g, 1.05 equivalent) and the bis-chloroformate of 1,3-propanediol of example 7 (90.0 g) were co-fed to a flask over 80 minutes. The temperature of the flask was maintained at 50° C. under a pressure of approximately 120 mm Hg during the addition period. The flask was then maintained at 50° C. for an additional 17 hours under vacuum (120 mm Hg).

Synthesis of Trimethylene Carbonate

A portion of the polycarbonate (79.6 g) with 1.5 g of added dibutyltindiacetate was cracked under vacuum. The flask was topped with a Vigreux distilling head. Distillate fractions were collected at:

1) 105–110° C. and 0.4 mm Hg (7.4 g, 10% trimethylene carbonate, pot temp. 194–213° C.), and
2) 110° C. and 0.4 mm Hg (59.5 g, 83% trimethylene carbonate, pot temp. 155–205° C.).

The overall recovery of trimethylene carbonate contained in the two distillate fractions, based on the polycarbonate charged, was 63% as determined by gas chromatography.

EXAMPLE 9

This is an example of the phosgene co-feed addition with 1,3-propanediol method of synthesizing a polycarbonate and subsequent conversion to trimethylene carbonate of the present invention. The equipment used was as described in example 7.

A flask was charged with 10.5 g of 1,3-propanediol. Next, additional 1,3-propanediol (65.6 g) and phosgene (94 g) were co-fed to the flask over the course of 2.5 hours. The reaction temperature was maintained at 15–38° C. using an ice bath. The stirred mixture was then heated and maintained at 50° C. for 17 hours with a nitrogen sparge to remove hydrogen chloride.

Synthesis of Trimethylene Carbonate

The crude polycarbonate tested positive for chloroformates using phosgene paper. The polycarbonate was catalyzed with 2 grams of dibutyltin diacetate and heated under vacuum as indicated. Using a Vigreux column, the following fractions were collected by distillation:

1) 116–118° C. and 2–3 mm Hg (3.1 g, 14.4% trimethylene carbonate)
2) 128–137° C. and 2–3 mm Hg (90 g, 91.7% trimethylene carbonate)

The overall recovery of trimethylene carbonate contained in the two distillate fractions, based on the polycarbonate charged, was 81% as determined by gas chromatography.

This example demonstrates that the bis-chloroformate does not need to be isolated. The polycarbonate can be made directly from phosgene and 1,3-propanediol. This example also illustrates that a nitrogen sparge in place of vacuum can be used to remove hydrogen chloride.

EXAMPLE 10

This is an example of the phosgene addition to 1,3-propanediol method of synthesizing a polycarbonate and subsequent conversion to trimethylene carbonate of the present invention. The equipment used was as described in example 7. The 1,2-dichloroethane is used as solvent.

Phosgene (49 g) was added over 50 minutes to a solution of 1,3-propanediol (40.7 g, 1.08 equivalent) in 1,2-dichloroethane (150 ml). The temperature was maintained at 5–25° C. during the addition period. A sample taken after the addition period showed that no phosgene was present and that the sample contained 8% trimethylene carbonate and other higher boiling materials. The crude reaction mixture was then warmed to 50° C. for two hours while sparging with nitrogen gas.

Using a Vigreux column, low boiling materials were stripped off at pot temperatures up to 170° C. using vacuum (5 mm Hg). Dibutyltindiacetate 1.52 g (1.7 wt. %) was then added as a cracking catalyst. Cracking of the oligomer took place at a pot temperature of 170–230° C. and head temperature of 124–134° C. at 2–3.5 mm Hg. 23 g of crude, 70% pure trimethylene carbonate was recovered, indicating an overall recovery of trimethylene carbonate of 29% as determined by gas chromatography.

This example shows that the use of a solvent does not improve the yield of trimethylene carbonate.

EXAMPLE 11

This is an example of the bis-chloroformate method of synthesizing a polycarbonate intermediate and subsequent conversion to trimethylene carbonate of the present invention. The bis-chloroformate was prepared as outlined in Example 7 and was 94.3% bis-chloroformate. The same equipment was used as in example 7.

The 1,3-propanediol (29.3 g, 1.05 equivalent) was added over 40 minutes to a pool of the bis-chloroformate of 1,3-propanediol (73.3 g). The temperature was maintained at 20° C. during the addition. A nitrogen sparge was used to remove hydrogen chloride. The flask was then warmed to 50° C. for five hours while maintaining the nitrogen sparge.

Dibutyltindiacetate (3.0 g) was then added. A Vigreux distillation head was utilized for distillation. The flask was heated under vacuum and distillate fractions were collected at:

1) 48–133° C. and 2 mm Hg (48.1 g, 84% trimethylene carbonate as measured by gas chromatography with a pot temperature of 125–200° C.).
2) 133–134° C. and 4 mm Hg (25.0 g, 55% trimethylene carbonate as measured by gas chromatography with a pot temperature of 200–210° C).

The overall recovery of trimethylene carbonate contained in the two distillate fractions, based on the polycarbonate charged was 73%.

This example demonstrates that good conversion is obtained when the reaction is conducted at moderate temperatures such as 50° C. Higher temperatures reduce the yield.

EXAMPLE 12

This is an example of the bis-chloroformate method of synthesizing a polycarbonate intermediate and subsequent conversion to trimethylene carbonate, including a heat treatment step, of the present invention. The bis-chloroformate was prepared as outlined in Example 7 and was 95% bis-chloroformate. The same equipment was used as in example 7.

A mixture of 1,3-propanediol (38.6 g, 1.03 equivalent) and the bis-chloroformate of 1,3-propanediol (99.3 g) were heated together under the following conditions and periods of time: 1) three hours at 50° C., 2) one hour at 100° C., and 3) 19 hours at 150° C. A subnatent nitrogen sparge was maintained to remove hydrogen chloride as it is formed.

The resulting polycarbonate tested negative for chloroformates using phosgene test paper. Phosgene test paper turns orange in the presence of chloroformates.

A portion of the polycarbonate was cracked under vacuum (without an added cracking catalyst). A Vigreux distillation head was utilized for distillation. The flask was heated under vacuum and distillate fractions were collected with a pot temperature of 233–243° C.:

1) 125–130° C. and 2.5 mm Hg (17.6 g, 85.4% trimethylene carbonate),
2) 130–145° C. and 2.5 mm Hg (48.2 g, 95.9% trimethylene carbonate), and
3) 145° C. and 2.8 mm Hg (15.2 g, 88.1% trimethylene carbonate).

The overall recovery of trimethylene carbonate contained in the three distillate fractions, based on the polycarbonate charged, was 80.1 g or 80% conversion.

This example demonstrates that the cracking step is effective even when a cracking catalyst is not used. Further, this example demonstrates that the heat treatment step provides polycarbonate that is substantially free of chloroformates and is therefore stable and non-corrosive.

The invention has been described with reference to the preferred embodiments. Obvious modifications and alterations will occur to others upon reading and understanding the detailed description. It is intended that the invention be construed as including all such modifications and alterations insofar as they come within the scope of appended claims or the equivalents thereof.

We claim:

1. A method of synthesizing trimethylene carbonate comprising the steps of:
   (a) reacting 1,3-propanediol and a compound selected from the group consisting of phosgene and bis-chloroformates to form a polycarbonate intermediate having the structure:

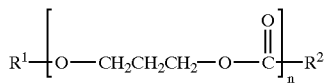

wherein n is at least 2; $R^1$ is an end group selected from the group consisting of H, $R^3$—Cl, $R^3$—OH and —C(O)Cl, where $R^3$ is $C_1$–$C_6$ linear or branched alkyl and $R^2$ is an end group selected from the group consisting of —OCH$_2$CH$_2$CH$_2$Cl, —OCH$_2$CH$_2$CH$_2$OH and Cl; and
   (b) providing a combination of temperature and pressure corresponding to vapor phase conditions for trimethylene carbonate.

2. The method of claim 1 wherein the polycarbonate intermediate has at least one —C(O)Cl end group and prior to step (b) the polycarbonate intermediate is heated to react and eliminate at least a portion of said chloroformate end groups.

3. The method of claim 1 further comprising (c) condensing the trimethylene carbonate vapors.

4. The method of claim 1 wherein the reactants and polycarbonate intermediate are sparged with an inert gas during (b).

5. The method of claim 1 wherein a reduced pressure is applied during (b).

6. The method of claim 4 wherein the inert gas comprises nitrogen.

7. The method of claim 1 wherein the temperature in (b) is between 50° C. and 250° C.

8. The method of claim 1 wherein (b) comprises depolymerizing the polycarbonate intermediate in the absence of catalyst.

9. The method of claim 1 wherein during the heating step (b), the temperature is greater than 150° C. and the pressure is less than 20 mm of mercury.

10. The method of claim 1 wherein a catalyst is used to facilitate depolymerizing the polycarbonate intermediate in (b).

11. The method of claim 10 wherein the catalyst is selected from the group consisting of zinc powder, zinc oxides, tin powder, tin halides and organo-tin compounds.

12. The method of claim 1 wherein the polycarbonate intermediate in (a) is formed by:
   (i) reacting 1,3-propanediol and phosgene, wherein the molar ratio of 1,3-propanediol to phosgene is from 1.3:0.7 to 0.7:1.3; and
   (ii) providing a temperature of −20° C. to 100° C. and maintaining the temperature for a period of time sufficient to react the 1,3-propanediol and phosgene to form the polycarbonate intermediate.

13. The method of claim 12 wherein the reactants and polycarbonate intermediate are sparged with an inert gas during (ii).

14. The method of claim 12 wherein a reduced pressure is applied to the reactor during (ii).

15. The method of claim 12 wherein the molar ratio of 1,3-propanediol to phosgene is from 1.05:0.95 to 0.95:1.05.

16. The method of claim 12 wherein the temperature of the reaction vessel in (ii) is from to 0° C. to 25° C.

17. The method of claim 12 wherein no solvent is used.

18. The method of claim 12 wherein an organic solvent, which does not contain active hydrogens, is added to the reactants in (i).

19. The method of claim 12 wherein a phosgene equivalent is used in place of phosgene.

20. The method of claim 19 wherein the phosgene equivalent is one or both of diphosgene or triphosgene.

21. The method of claim 1 wherein the polycarbonate intermediate in (a) is formed by:
   (i) reacting 1,3-propanediol with an excess of phosgene, at a temperature of from −20° C. to 100° C., to form a bis-chloroformate having the structure:

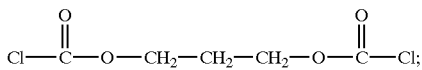

(ii) reacting 1,3-propanediol with the bis-chloroformate such-that the molar ratio of 1,3-propanediol to the bis-chloroformate is from 1.3:0.7 to 0.7:1.3; and
   (iii) providing a temperature of 0° C. to 100° C. and maintaining the temperature for a period of time sufficient to react the 1,3-propanediol and bis-chloroformate to form the polycarbonate intermediate.

22. The method of claim 21 wherein the reactor is sparged with an inert gas during (iii).

23. The method of claim 21 wherein a reduced pressure is applied to the reactor during (iii).

24. The method of claim 21 wherein the molar ratio of 1,3-propanediol to bis-chloroformate is from 1.05:0.95 to 0.95:1.05.

25. The method of claim 21 wherein the temperature of the reaction vessel in (i) is from to 0° C. to 25° C.

26. The method of claim 21 wherein the temperature in (iii) is from to 25° C. to 75° C.

27. The method of claim 21 wherein no solvent is used.

28. The method of claim 21 wherein an organic solvent, which does not contain active hydrogens, is added to the reactants in (i).

29. The method of claim 22 wherein the inert gas comprises nitrogen.

30. The method of claim 21 wherein a phosgene equivalent is used in place of phosgene.

31. The method of claim 30 wherein the phosgene equivalent is one or both of diphosgene or triphosgene.

32. The method of claim 1 further comprising (d) isolating the condensed trimethylene carbonate; and (e) crystallizing the trimethylene carbonate in a suitable organic solvent.

33. The method of claim 32 wherein the organic solvent is acetone.

34. The method of claim 1 wherein the condensed trimethylene carbonate is placed in a suitable vessel and is allowed to solidify.

35. The method of claim 34 wherein the vessel is a drum or a tote.

36. The method of claim 1 wherein the condensed trimethylene carbonate is solidified.

37. The method of claim 36 wherein the solidified trimethylene carbonate is milled into granular or powder form.

* * * * *